(12) United States Patent
Xu et al.

(10) Patent No.: US 9,949,887 B2
(45) Date of Patent: Apr. 24, 2018

(54) METHOD, DEVICE AND HELMET FOR GUIDING THE BLIND (71) Applicant: CLOUDMINDS (SHENZHEN) ROBOTICS SYSTEMS CO., LTD., Beijing (CN)

(72) Inventors: Zeyuan Xu, Beijing (CN); Bin Wang, Beijing (CN)

(73) Assignee: CLOUDMINDS (SHENZHEN) ROBOTICS SYSTEMS CO., LTD., Beijing (CN)

( * ) Notice: Subject to any disclaimer, the term of this patent is extended or adjusted under 35 U.S.C. 154(b) by 0 days.

(21) Appl. No.: 15/722,731

(22) Filed: Oct. 2, 2017

(65) Prior Publication Data

US 2018/0021207 A1 Jan. 25, 2018

Related U.S. Application Data

(63) Continuation of application No. PCT/CN2016/106020, filed on Nov. 16, 2016.

(30) Foreign Application Priority Data

Nov. 16, 2015 (CN) .......................... 2015 1 0783615

(51) Int. Cl.
| | |
|---|---|
| *G09B 21/00* | (2006.01) |
| *A61H 3/06* | (2006.01) |
| *A61F 9/08* | (2006.01) |
| *A61H 23/02* | (2006.01) |
| *A42B 3/30* | (2006.01) |

(52) U.S. Cl.
CPC .............. *A61H 3/061* (2013.01); *A42B 3/30* (2013.01); *A61F 9/08* (2013.01); *A61H 23/0263* (2013.01); *G09B 21/003* (2013.01); *A61H 2003/063* (2013.01); *A61H 2201/5007* (2013.01)

(58) Field of Classification Search
CPC ................ G09B 21/03; G01C 21/3691; G01C 21/3407; A61H 3/061
USPC ........................................................ 340/4.1
See application file for complete search history.

(56) References Cited

U.S. PATENT DOCUMENTS

| | | | |
|---|---|---|---|
| 5,807,111 A | 9/1998 | Schrader | |
| 8,627,839 B1 * | 1/2014 | Martinez .................. | A45B 3/00 135/66 |
| 2013/0201308 A1 * | 8/2013 | Tan ........................ | G09B 21/00 348/62 |

FOREIGN PATENT DOCUMENTS

| | | |
|---|---|---|
| CN | 103735395 A | 4/2014 |
| CN | 203694028 U | 7/2014 |
| CN | 204601068 U | 9/2015 |
| CN | 105250119 A | 1/2016 |

(Continued)

OTHER PUBLICATIONS

The Written Opinion of the International Searching Authority dated Feb. 23, 2017; PCT/CN2016/106020.

*Primary Examiner* — Vernal Brown
(74) *Attorney, Agent, or Firm* — Ladas & Parry LLP (57) ABSTRACT

A method for guiding the blind includes: determining a target direction; and controlling a mechanical device to shift its center of gravity toward the target direction according to the target direction; wherein the mechanical device comprises a balance weight, a connecting rod, and a rotating axis, the connecting rod is connected to the rotating axis, and the balance weight is located on the connecting rod.

18 Claims, 9 Drawing Sheets

(56) References Cited

FOREIGN PATENT DOCUMENTS

GB 2345628 A 7/2000
JP 2004-008748 A 1/2004

* cited by examiner

FIG. 12

METHOD, DEVICE AND HELMET FOR GUIDING THE BLIND

TECHNICAL FIELD

The present invention relates to intelligent apparatus technical field, and more particularly, to a method, device, and apparatus for guiding the blind.

BACKGROUND

Due to visual defect, it is always inconvenient for the blind to go out. To meet living needs of the blind, various blind guiding apparatuses emerge. At present, most of the blind guiding apparatuses sense the surroundings via various sensors, calculate reasonable routes to avoid road obstacles, and guide users to move forward via voice commands (such as turning left, turning right, etc.).

When an intelligent blind guiding apparatus guides a user to move forward via voice commands, it takes a long process time from receiving a voice command to understanding the voice command, and finally to executing the voice command. Hence, it is inefficient.

The prior art has a disadvantage as follows.

With low guiding efficiency, the existing blind guiding apparatuses guide users to walk ahead via voice commands.

SUMMARY

A method for guiding the blind is provided in an embodiment of the present disclosure. The method includes: determining a target direction; and controlling a mechanical device to shift its center of gravity toward the target direction according to the target direction; wherein the mechanical device comprises a balance weight, a connecting rod, and a rotating axis, the connecting rod is connected to the rotating axis, and the balance weight is located on the connecting rod.

A device for guiding the blind is provided in another embodiment of the present disclosure. The device includes a first determining module for determining a target direction; and a first controlling module for controlling a mechanical device to shift its center of gravity toward the target direction according to the target direction, wherein the mechanical device comprises a balance weight, a connecting rod, and a rotating axis, the connecting rod is connected to the rotating axis, and the balance weight is located on the connecting rod.

A blind guiding helmet is provided in still another embodiment of the present disclosure. The blind guiding helmet includes a first determining module for determining a target direction; and a first controlling module for controlling a mechanical device to shift its center of gravity toward the target direction according to the target direction; wherein the mechanical device comprises a balance weight, a connecting rod, and a rotating axis, the connecting rod is connected to the rotating axis, and the balance weight is located on the connecting rod.

BRIEF DESCRIPTION OF THE DRAWINGS

The specific embodiments of the present invention are described with reference to attached drawings as follows, wherein.

wherein, 1. facing direction; 2. connecting rod; 3. rotating axis; 4. balance weight.

DETAILED DESCRIPTION

To make the technical solutions and advantages of the present invention more apparent and explicit, explanations are further elaborated with reference to the exemplary embodiments of the present invention as follows. Obviously, the described embodiments are only part of the embodiments of the present invention, rather than exhaustion of all the embodiments. Moreover, the embodiments of the present invention, as well as the features therein, can be combined with each other if they do not conflict with each other.

In the process of invention, the inventor takes notice of problems.

The existing blind guiding apparatuses that guide users to move ahead via voice have disadvantages as follows:

1) it is difficult to quantify direction change indicated by voice commands; for example, it is difficult to describe accurate angles of left turn and right turn with commands such as turning left, turning right, etc.; even if the voice commands include information on accurate angles, it is still difficult for the users to accurately execute the voice commands.

2) as the voice commands are vulnerable to interference of ambient noise, the users are apt to make mistakes in comprehension; moreover, it is hard to remind the users repeatedly; once mistakes in comprehension happen, it takes a more complex process to correct the mistakes after execution of wrong commands.

Against these disadvantages of the prior art, the embodiments of the present invention provide a method, device, and apparatus for guiding the blind, and make explanations as follows.

Figure 1:
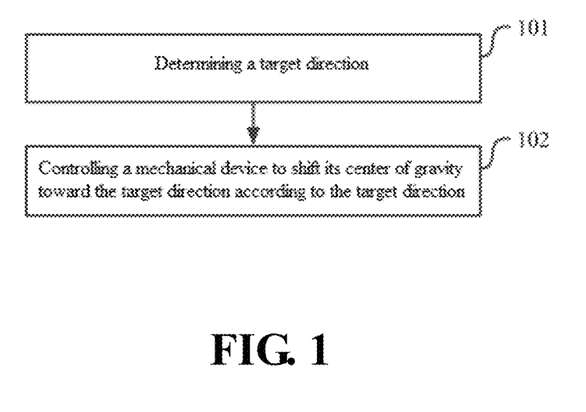
FIG. 1 is a flow diagram of implementation of a method for guiding the blind in the embodiments of the present invention.

FIG. 1 is a flow diagram of implementation of a method for guiding the blind in the embodiments of the present invention. As shown in the figure, the method for guiding the blind may comprise steps as follows:

Step 101, determining a target direction;

Step 102, controlling a mechanical device to shift its center of gravity toward the target direction according to the target direction.

In the embodiment of the present invention, after the target direction is determined, the mechanical device can be controlled to shift its center of gravity toward the target direction according to the target direction. In the specific implementation, the center of gravity can be directly shifted to the target direction. For example, suppose the target direction is 20° north by west, then, the mechanical device can be controlled to shift its center of gravity to 20° north by west. Alternatively, the center of gravity can be shifted to get substantial close to the target direction. For example, suppose the target direction is due left, then the mechanical device can be controlled to shift left by 30°. The user can feel center of gravity shift, and adjust his advancing direction according to the indicated direction of the center of gravity shift. In the course of the adjustment, the mechanical device is controlled to ensure that its center of gravity is shifted to approach the target direction.

The embodiments of the present invention indicate the target direction in a shifting manner of the center of gravity. Since people usually walk in an advancing direction consistent with the head orientation, indications of turning head of the blind to the target direction can make it efficient for them to find the target direction. In addition, due to a support structure on their necks and pressure upon their scalps in different directions, the blind can easily feel center of gravity deviation, thereby determining the target direction efficiently.

The method for guiding the blind provided in the embodiments of the present invention can indicate the advancing direction by changing a center of gravity position on a headset apparatus. Compared with the existing indication manner of voice commands, it does not take the user some time to understand meanings of the voice commands; instead, shifting mechanism of centre of gravity can help the user to feel direction indications directly, providing real-time feedbacks after the blind changes a direction, and providing instructions to the blind to adjust the direction, thereby indicating the advancing direction for the blind accurately and efficiently, and improving the blind guiding efficiency.

During the implementation, to be specific, said determining a target direction may be:

detecting a current position of a user;

determining the target direction according to the current position of the user and a target position choosed by the user.

In the specific implementation, the target position determined by the user can be received in advance, and an advancing route is planned out according to an initial position and the target position, and then is stored locally; in the course of the user's advance, the current position of the user is determined in real time to calculate a next advancing direction; alternatively, in the course of the user's advance, the target position choosed by the user is received at any time to determine the target direction according to the target position choosed by the user and the current position.

Wherein, the user can determine the target position where the user desires to go, i.e., destination, in an operating manner of voice or control keys. To be specific, said detecting a current position of a user can be realized by the existing positioning technology, which is not elaborated in the present invention.

It needs to be explained that the embodiments of the present invention do not limit the sequence of receiving the target position determined by the user and detecting the current position of the user in the course of the user's advance.

The target direction in the embodiments of the present invention may be determined locally. A user side directly detects the current position of the user and determines the target direction, which can ensure that indications of directions are still available to the user in the absence of communication with the outside world, save power consumption to a certain degree, and achieve the purpose of high-efficient blind guiding.

During the implementation, to be specific, said determining a target direction may be:

receiving a blind guiding command sent by a blind guiding system, the blind guiding command comprising the target direction.

In the specific implementation, the user side can receive a blind guiding command sent by an intelligent blind guiding system; the blind guiding command may include the target direction, i.e., the target direction can be sent by the blind guiding system to the user side; the blind guiding system can position the current position of the user automatically, and send the blind guiding command including planned advancing directions to the user side according to the current position of the user and a preset route; after an external command is received, the target direction is determined according to the external command.

The target direction in the embodiments of the present invention may be determined by an external system sending a command, without much calculation or other operations on the user side, thus the amount of storage and calculation of the user side is reduced; moreover, the blind guiding system usually possesses greater calculation power and storage capacity than the user side, and therefore can send the command including the planned advancing directions to the user in a real-time, fast, and accurate manner; the blind guiding system sends the command with better real-time characteristic and higher accuracy, thereby further improving the blind guiding efficiency.

During the implementation, prior to said receiving a blind guiding command sent by a blind guiding system, the method may further comprise:

receiving a blind guiding request sent by the user, the blind guiding request comprising a target position;

sending the target position to the blind guiding system.

In the course of the user' advance, the user sends the blind guiding request in a manner of voice or control keys. The blind guiding request includes the target position. After receiving the blind guiding request of the user, the user side sends the target position to the blind guiding system. The intelligent blind guiding system can plan out the advancing route for the user according to the target position and the current position of the user, and calculate the next direction (i.e., the target direction) in which the user should advance according to the route and the current position of the user.

Wherein, the current position of the user can be either obtained by automatic positioning of the intelligent blind guiding system, or detected by the user side and then sent to the blind guiding system.

In the embodiments of the present invention, the target position sent by the user can be received at any time; after the blind guiding system determines the target direction, the user is instructed to walk; thus, the user experience is further improved.

During the implementation, to be specific, the mechanical device may include a balance weight, a connecting rod, and a rotating axis, the connecting rod is connected to the rotating axis, and the balance weight is located on the connecting rod.

In the specific implementation, the mechanical device may include three parts: a balance weight, a connecting rod, and a rotating axis. The connecting rod is connected to the rotating axis. To be specific, one end of the connecting rod may be connected to the rotating axis; alternatively, a center of the connecting rod may be connected to the rotating axis, such that the connecting rod can centre around the rotating axis. The balance weight is mounted on the connecting rod. The balance weight may either be fixedly mounted or be movable on the connecting rod.

During the implementation, one end of the connecting rod may be connected to the rotational axis; to be specific, said controlling a mechanical device to shift its center of gravity may be controlling orientation of the connecting rod that centers around the rotating axis.

In the specific implementation, one end of the connecting rod may be connected to the rotational axis; the connecting rod can rotate around one end that is connected to the rotating axis; to be specific, said controlling a mechanical device to shift its center of gravity may be controlling the orientation of the connecting rod.

For example, when the target direction is 50° east by south, the connecting rod can be controlled to centre around the rotating axis to 50° east by south. Since the balance weight is located on the connecting rod, the user can feel that the centre of gravity deviation of the mechanical device is 50° east by south, thereby turning his head/body to 50° east by south, and advancing in the direction.

To limit the angle range of the rotation of the connecting rod, the embodiments of the present invention may further be implemented in a manner as follows.

During the implementation, to be specific, said controlling orientation of the connecting rod that centers around the rotating axis may be controlling the connecting rod to shift toward the target direction in a preset angle range.

Suppose the target direction is due east, and the preset angle range is within 30°. Whatever direction the user faces currently, the embodiments of the present invention can control the connecting rod to shift eastward by 30°. If the user still does not face due east after adjusting eastward by 30°, then the connecting rod can be controlled to go on shifting eastward by one or more 30° until the connecting rod finally faces the target direction.

The embodiments of the present invention limit the rotation angle of the connecting rod, and indicate the target direction in a manner of gradual shifting, thereby avoiding 360° rotation of the connecting rod, both reducing the complexity of the design and improving the durability of the connecting rod and the rotating axis.

During the implementation, a center of the connecting rod is connected to the rotating axis; to be specific, said controlling a mechanical device to shift its center of gravity may be controlling the balance weight to be located at one end of the center of the connecting rod.

In the embodiments of the present invention, as the center of the connecting rod is connected to the rotating axis, the center of gravity shift can be controlled by placing the balance weight at one end of the center of the connecting rod to achieve the purpose of indicating directions for the user.

For example, if an included angle between the target direction and a left end of the center of the connecting rod is relatively small, then the balance weight can be controlled to slide to the left end of the center of the connecting rod. If an included angle between the target direction and a right end of the center of the connecting rod is relatively small, then the balance weight can be controlled to slide to the right end of the center of the connecting rod.

The embodiments of the present invention can control the shifting of center of gravity of the mechanical device by controlling the balance weight to be on which end of the center of the connecting rod, and can indicate the advancing direction for the user without the connecting rod rotating around the rotating axis.

During the implementation, the method further comprises:

determining a current advancing direction of the user;

controlling a distance from the balance weight to a joint between the connecting rod and the rotating axis according to relation between the current advancing direction of the user and the target direction.

In the specific implementation, the balance weight can slide on the connecting rod. The method for guiding the blind can further determine the current advancing direction of the user, and control the position where the balance weight slides on the connecting rod according to the relation between the current advancing direction and the target direction. For example:

if one end of the connecting rod is connected to the rotating axis, there may exist circumstances as follows:

when the current advancing direction gets closer and closer to the target direction in the process of the user's adjustment, the balance weight can be controlled to move farther and farther from the other end to decrease weight gradually, such that the user feels change in the weight, and is reminded that the adjustment of the direction is correct;

when the current advancing direction gets farther and farther from the target direction in the process of the adjustment, the balance weight can be controlled to get closer and closer to the other end to increase weight gradually, such that the user feels change in the weight, and is reminded that the adjustment of the direction is wrong;

when the current advancing direction is totally opposite to the target direction, the balance weight can be controlled to slide to the other end of the connecting rod to increase weight, such that the user feels remarkable center of gravity deviation.

The embodiments of the present invention can control the position where the balance weight slide on the connecting rod according to the relation between the current advancing direction and the target direction, can indicate whether directions are correct for the user with different weights when the user adjusts the directions according to conditions shifting of the center of gravity, thereby further improving the user experience.

Besides, if the center of the connecting rod is connected to the rotating axis, the distance between the balance weight and the center of the connecting rod may also be controlled according to the degree of the angle formed by the target direction and the current advancing direction to indicate the degree of closeness between the current advancing direction of the user and the target direction.

For example, if the target direction is 30° left from the current advancing direction, the balance weight can be controlled to slide to a position on the left, 2 centimeters from the center of the current advancing direction; if the target direction is 90° left from the current advancing direction, the balance weight can be controlled to slide to a position on the left, 5 centimeters from the center of the current advancing direction.

In the embodiments of the present invention, head rotation conditions may be detected via a gravity sensor or an electronic compass to determine the current advancing direction; alternatively, the current advancing direction of the user may be determined via other devices, which is not limited in the present invention.

The embodiments of the present invention can indicate the degree of closeness (or the degree of the included angle) between the current advancing direction of the user and the target direction by controlling the distance between the balance weight and the center of the connect rod, thereby improving the user experience to some degree.

During the implementation, to be specific, said controlling a distance from the balance weight to a joint between the connecting rod and the rotating axis according to relation between the current advancing direction of the user and the target direction may be:

controlling the balance weight to slide to the joint between the connecting rod and the rotating axis when the current advancing direction of the user is consistent with the target direction.

In the specific implementation, the balance weight can be controlled to slide to a central position (which can be interpreted as locating the balance weight on the top of the head), i.e., the joint between the connecting rod and the rotating axis, when the current advancing direction is consistent with the target direction; at this moment, the user can feel no center of gravity deviation on the head, such that the user can move forward normally, without feeling pressure upon his scalp.

The embodiments of the present invention can control the balance weight to slide to the central position when the current advancing direction is consistent with the target direction, such that the user will not feel forward center of gravity deviation that tilts the head, thereby further improving the user experience.

Based on the same inventive concept, the embodiments of the present invention further provide a device for guiding the blind. Since the principles how the device solve problems are similar to those of the method for guiding the blind, for the implementation of the device, see that of the method, which is not elaborated herein.

Figure 2:
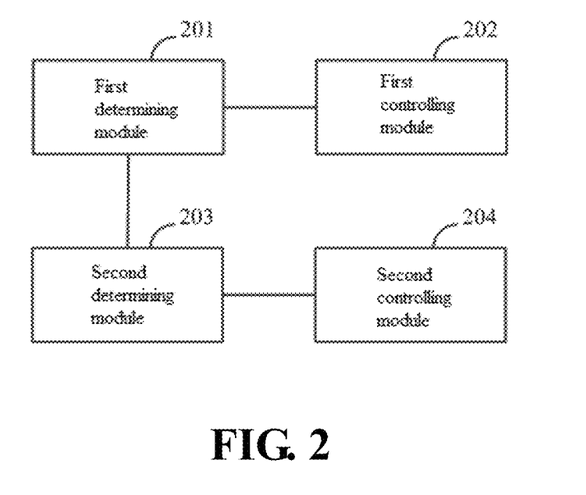
FIG. 2 is a structure diagram of a device for guiding the blind in the embodiments of the present invention.

FIG. 2 is a structure diagram of a device for guiding the blind in the embodiments of the present invention. As shown in the figure, the device for guiding the blind may comprise:

a first determining module 201 for determining a target direction;

a first controlling module 202 for controlling a mechanical device to shift its center of gravity toward the target direction according to the target direction.

During the implementation, to be specific, the first determining module may comprise:

a detecting unit for detecting a current position of a user;

a direction determining module for determining the target direction according to the current position of the user and a target position choosed by the user.

During the implementation, to be specific, the first determining module may be used for receiving a blind guiding command sent by a blind guiding system, the blind guiding command including the target direction.

During the implementation, the device may further comprise:

a request receiving module for receiving a blind guiding request sent by the user, the blind guiding request including a target position;

a sending module for sending the target position to the blind guiding system.

During implementation, to be specific, the mechanical device may comprise a balance weight, a connecting rod, and a rotating axis, the connecting rod is connected to the rotating axis, and the balance weight is located on the connecting rod.

During the implementation, one end of the connecting rod is connected to the rotational axis; to be specific, the first controlling module may be used for changing center of gravity deviation of the mechanical device by controlling orientation of the connecting rod that centers around the rotating axis.

During the implementation, to be specific, the first controlling module may be used for controlling the connecting rod that centers around the rotating axis to shift toward the target direction in a preset angle range.

During the implementation, a center of the connecting rod is connected to the rotating axis; to be specific, the first controlling module may be used for changing center of gravity deviation of the mechanical device by controlling the balance weight to be located on one end of the connecting rod by the center.

During the implementation, the device may further comprise:

a second determining module 203 for determining a current advancing direction of the user;

a second controlling module 204 for controlling a distance from the balance weight to a joint between the connecting rod and the rotating axis according to relation between the current advancing direction of the user and the target direction.

During the implementation, to be specific, the second controlling module may be used for controlling the balance weight to slide to the joint between the connecting rod and the rotating axis when the current advancing direction of the user is consistent with the target direction.

In the above embodiments, the existing functional elements can be used for the implementation. For example, the existing direction determining elements can be used as the first determining module and the second determining module. At least, the voice blind guiding apparatuses in the existing blind guiding technology possess elements for performing the function. Regarding the first controlling module and the second controlling module, they are elements in any apparatuses that possess the controlling function, and are available to persons skilled in the art through corresponding design and development.

For the convenience of description, all the components of the device are divided into various modules or units according to functions, and are separately described. Certainly, when the present invention is carried out, the functions of these modules or units can be achieved in one or more hardware or software.

Based on the same inventive concept, the embodiments of the present invention further provide an apparatus for guiding the blind, and make explanations as follows.

Figure 3:
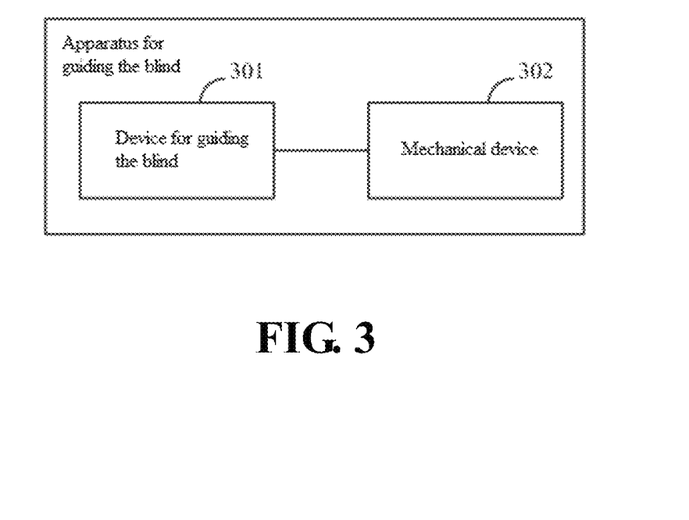
FIG. 3 is a structure diagram of an apparatus for guiding the blind in the embodiments of the present invention.

FIG. 3 is a structure diagram of an apparatus for guiding the blind in the embodiments of the present invention. As shown in the figure, the apparatus for guiding the blind may comprise a device for guiding the blind 301 and a mechanical device 302.

In the embodiments of the present invention, the device for guiding the blind may control the mechanical device to adjust its center of gravity after determining a target direction, to indicate directions for the user.

In the specific implementation, the mechanical device may be a device including a rotating axis, a connecting rod, and a balance weight.

In the embodiments of the present invention, the reason for adopting a combination of a rotating axis, a connecting rod, and a balance weight is that the combination is a customary and mainstream manner, and can be easily used and understood by persons skilled in the art. Hence, the embodiments of the present invention is illustrated by the combination of the rotating axis, the connecting rod, and the balance weight as example. However, in theory, other manners are also viable, e.g., a ball rolling in a slideway, as long as the purpose of adjusting the center of gravity can be achieved in these means. The combination of the rotating axis, the connecting rod, and the balance weight merely serves to teach persons skilled in the art how to specifically carry out the present invention, but it does not mean that the combination of the rotating axis, the connecting rod, and the balance weight is the unique manner. During the implementation, corresponding means can be determined according to practical needs.

In the embodiments of the present invention, the apparatus for guiding the blind may be an apparatus worn on head, such as a helmet, a hat, etc.; when wearing on his head the apparatus for guiding the blind, the user can directly feel center of gravity change of the apparatus for guiding the blind, following the change to adjust his body, thereby finding the target direction, without reading voice commands or spending some time understanding the commands; thus, the apparatus for guiding the blind as provided by the embodiments of the present invention can facilitate the user to find the target direction as efficiently as possible, and improve the blind guiding efficiency remarkably.

To facilitate the implementation of the present invention, instances are provided for explanations as follows.

Embodiment 1

Figure 4:
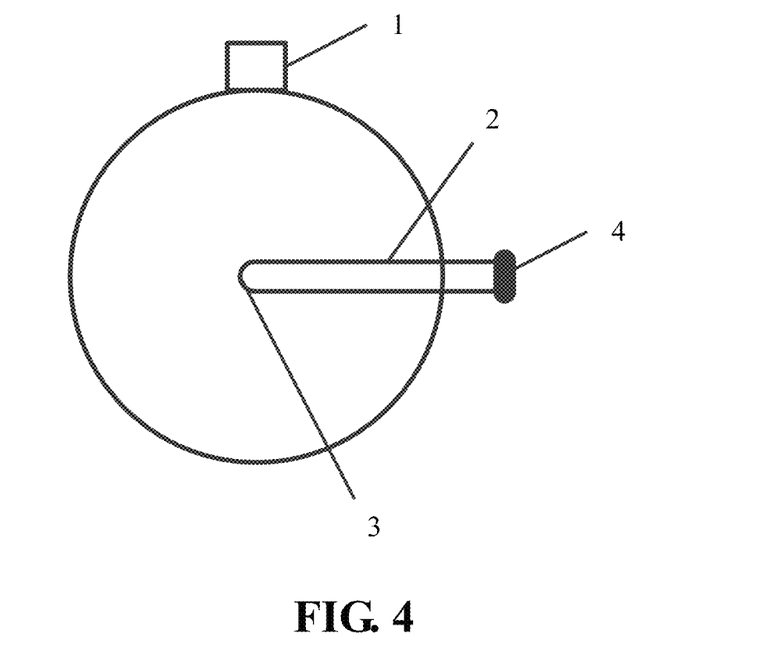
FIG. 4 is a first schematic diagram from the top of an apparatus for guiding the blind in the embodiments of the present invention.

FIG. 4 is a first schematic diagram from top of an apparatus for guiding the blind in the embodiments of the present invention. As shown in the figure, the user can wear the apparatus for guiding the blind on his head. In the figure, a protrusion part 1 may refer to orientation of face; a connecting rod 2 is pivotally connected to a rotating axis 3; the connecting rod 2 can centre around the rotating axis 3, a balance weight 4 can slide on the connecting rod 2.

Figure 5:
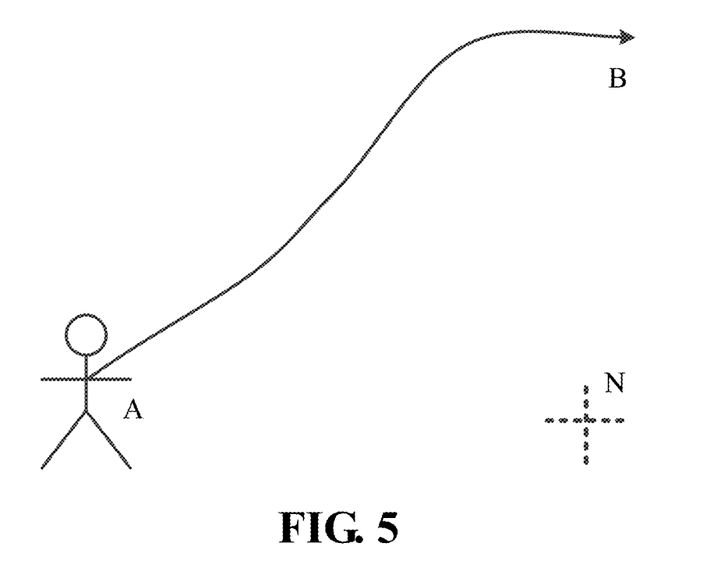
FIG. 5 is a diagram of a blind guiding scene in the embodiments of the present invention.

FIG. 5 is a diagram of a blind guiding scene in the embodiments of the present invention. As shown in the figure, suppose the current position of a blind user is Point A, the place he desires to go (i.e., the destination) is Point B, and the top of the figure refers to due north.

Figure 6:
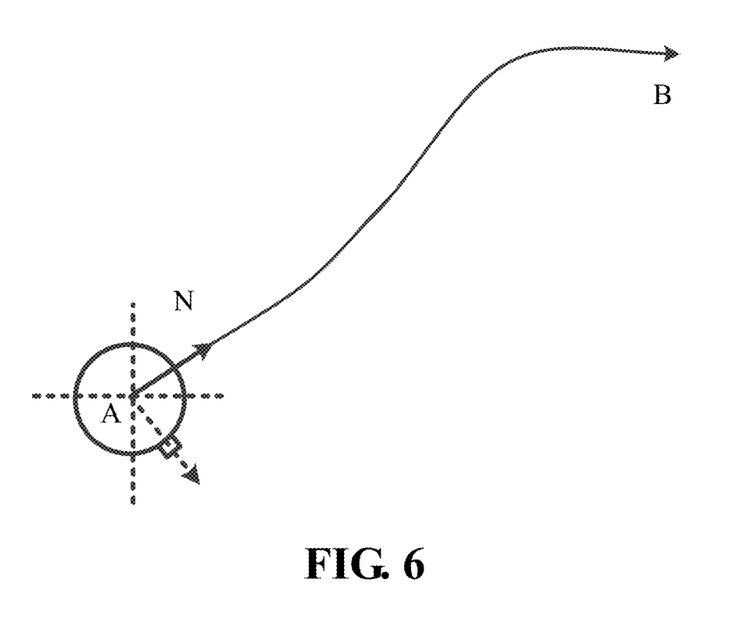
FIG. 6 is a diagram of an initial state of an apparatus for guiding the blind in the embodiments of the present invention.

FIG. 6 is a diagram of an initial state of an apparatus for guiding the blind in the embodiments of the present invention. As shown in the figure, suppose the blind user faces 45° east by south (the direction to which the dotted-line arrow in the figure points). Suppose an external command is received at this moment, the command indicates that the target direction is 30° east by north (the direction to which the solid-line arrow in the figure points).

After determining that the target direction is 30° east by north, the apparatus for guiding the blind controls the mechanical device to shift its center of gravity to 30° east by north.

Figure 7:
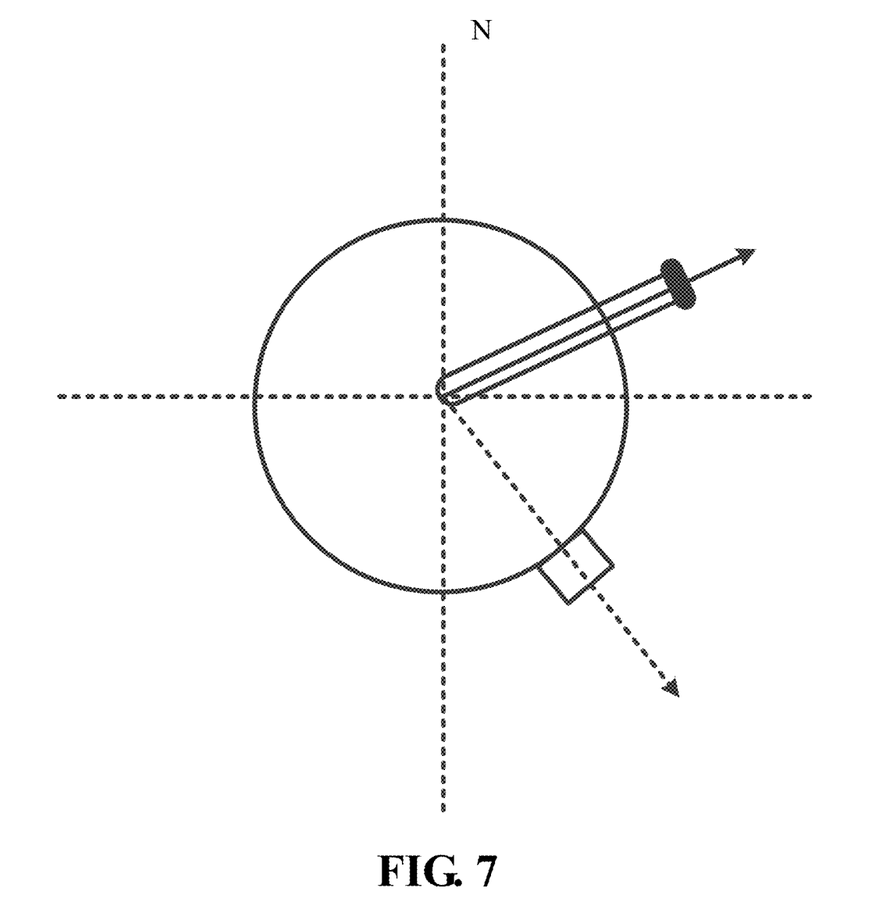
FIG. 7 is a structure diagram of a connecting rod in shifting in the embodiments of the present invention.

FIG. 7 is a structure diagram of a connecting rod in shifting in the embodiments of the present invention. As shown in the figure, the apparatus for guiding the blind can control the connecting rod to rotate around the rotating axis to 30° east by north, control the balance weight to be located at the end of the connecting rod, thereby enabling the blind to feel pressure at 30° east by north, and achieving the purpose of indicating the advancing direction for the blind.

The blind user can change a direction according to the pressure that he feels upon his head, and the direction to which the center of gravity of the apparatus for guiding the blind points can be adjusted constantly in the course of changing the direction, to ensure that it points to 30° east by north.

Figure 8:
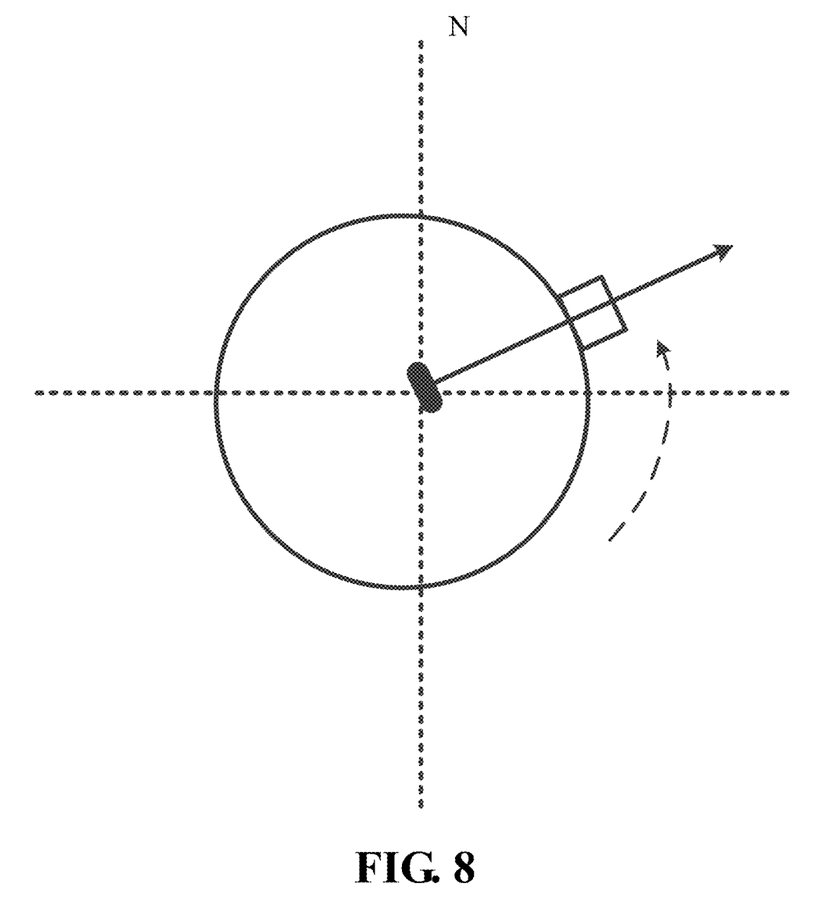
FIG. 8 is a diagram of a final state of an apparatus for guiding the blind in the embodiments of the present invention.

FIG. 8 is a diagram of a final state of an apparatus for guiding the blind in the embodiments of the present invention. As shown in the figure, the direction that the blind face is consistent with the target direction, i.e., both are 30° cast by north. At this moment, the apparatus for guiding the blind in the embodiments of the present invention can return the balance weight to the central position, keeping the heads of the blind from influence of the deviating pressure when they walk in the correct direction, thereby improving the user experience of the blind.

Embodiment 2

Figure 9:
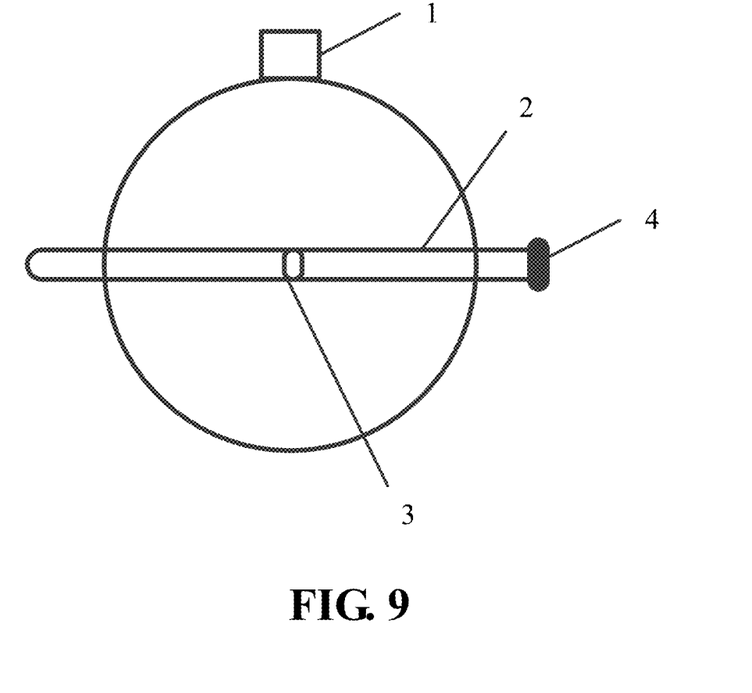
FIG. 9 is a second schematic diagram from the top of an apparatus for guiding the blind in the embodiments of the present invention.

FIG. 9 is a second schematic diagram from top of an apparatus for guiding the blind in the embodiments of the present invention. As shown in the figure, the user can wear the apparatus for guiding the blind on his head. In the figure, a protrusion part 1 may refer to an orientation of face; a connecting rod 2 is connected to a rotating axis 3; the connecting rod 2 can centre around the rotating axis 3; a balance weight 4 can slide on the connecting rod 2.

Figure 10:
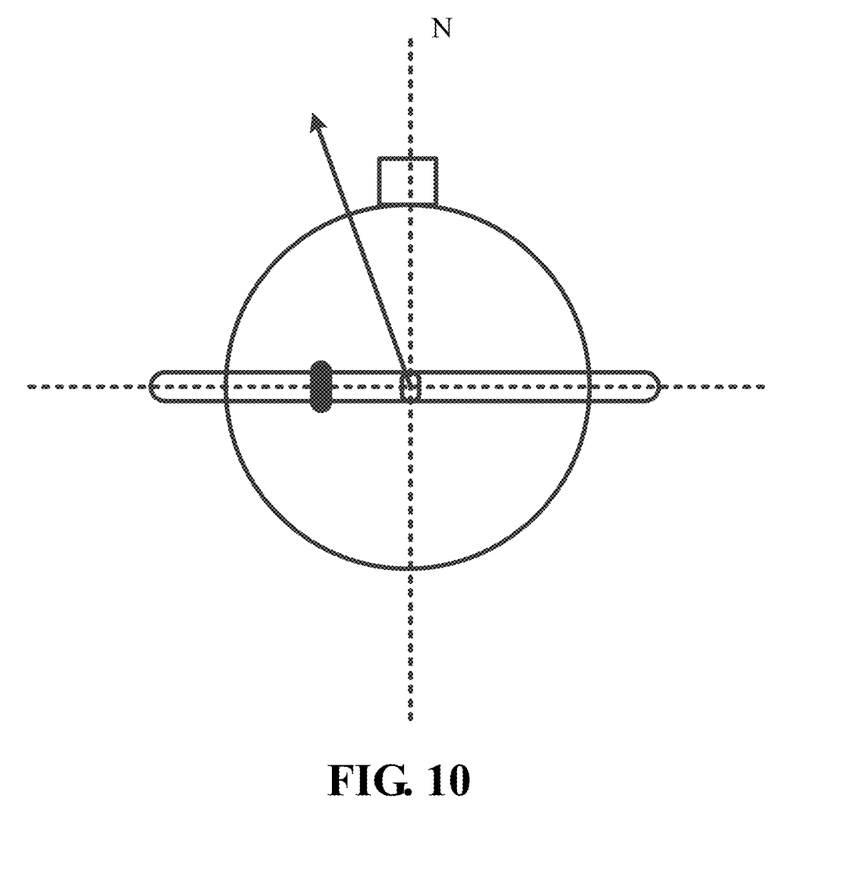
FIG. 10 is a structure diagram of a balance weight during indication in the embodiments of the present invention.

FIG. 10 is a structure diagram of a balance weight during indication in the embodiments of the present invention. As shown in the figure, suppose the blind user faces due north, an external command is received at this moment, and the command indicates that the target direction is 30° north by west (the direction to which the solid-line arrow in the figure points).

The apparatus for guiding the blind can control the balance weight to slide to a position on the left, 3 centimeters from the center of the connecting rod, such that the blind can feel that his head slightly deviates left, then adjusts the advancing direction to slightly shift left, thereby achieving the purpose of indicating the advancing direction for the blind user.

If the target direction is 90° north by west, the apparatus for guiding the blind can control the balance weight to slide to the far left end of the center of the connecting rod, such that the blind user can feel that his head obviously deviates left, and then adjusts the advancing direction to face left, thereby achieving the purpose of indicating the advancing direction for the blind user.

Figure 11:
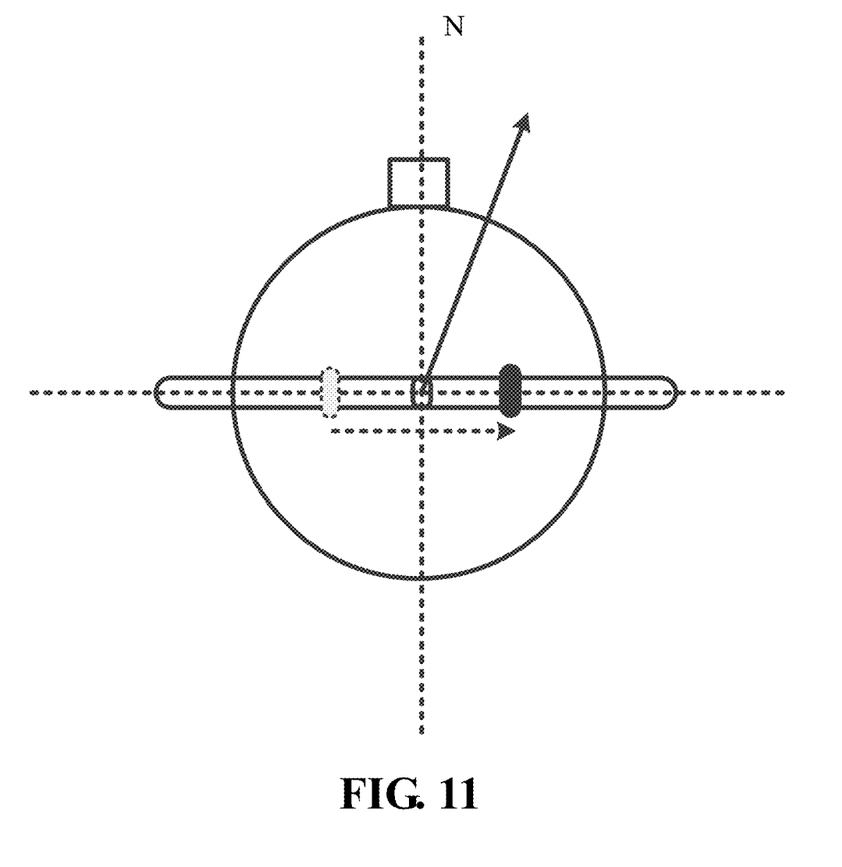
FIG. 11 is a structure diagram of a balance weight during slide in the embodiments of the present invention.

FIG. 11 is a structure diagram of a balance weight during sliding in the embodiments of the present invention. As shown in the figure, if the target direction is 30° north by east, the apparatus for guiding the blind can control the balance weight to slide to a position on the right, 3 centimeters from the center of the connecting rod, such that the blind user can feel that his head deviates right, and then adjusts the advancing direction to shift right, thereby achieving the purpose of indicating the advancing direction for the blind user.

When the advancing direction is consistent with the target direction, the balance weight can return to the joint between the connecting rod and the rotating axis, i.e., the blind can feel weight back on the top of his head, without deviation. At this moment, the blind can judge that the direction is correct, and move forward normally.

Embodiment 3

The apparatus for guiding the blind in the embodiment of the present invention may be an annulus that the user wears on his shoulder or waist, and is explained as follows.

Figure 12:
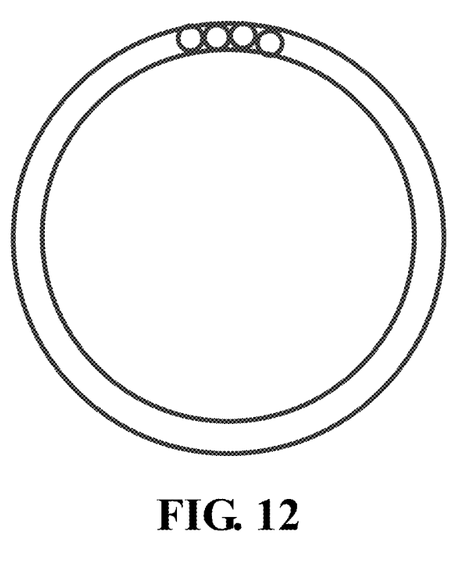
FIG. 12 is a third schematic diagram from the top of an apparatus for guiding the blind in the embodiments of the present invention.

FIG. 12 is a third schematic diagram from top of an apparatus for guiding the blind in the embodiments of the present invention. As shown in the figure, suppose the apparatus for guiding the blind is an apparatus (similar to a belt) that can be worn on the waist, the mechanical device may comprise a circular slideway and a ball. In FIG. 12, the position of the ball may refer to the position where the belly of the user is.

In the embodiments of the present invention, after determining the target direction, the apparatus for guiding the blind can control the ball to slide along the circular slideway to the target direction. The direction vector from the center (also referred to as the center of circle) of the circular slideway to the ball is the target direction. The user can adjust his advancing direction after feeling the deviation of the weight on the waist.

In the specific implementation, there may be multiple balls, and the distribution of the balls is controlled according to the current advancing direction and the target direction.

When the current advancing direction is not consistent with the target direction, the multiple balls are all driven to slide to the position consistent with the target direction. Since the multiple balls are at the same place, the user can obviously feel that the weight on the waist deviates to the target direction, thereby determining the next advancing direction, and adjusting his orientation.

When the current advancing direction is consistent with the target direction, the multiple balls can be uniformly distributed in the circular slideway, such that the user feels a balance of the weight on his waist, without any deviation.

In the process of the adjustment, the positions of the multiple balls are changed in the circular slideway according to the degree of closeness between the current advancing direction and the target direction. The closer to the target direction, the weaker weight deviation the user feels; the farther from the target direction, the stronger weight deviation the user feels.

For example, suppose there are four balls, when the current advancing direction is not consistent with the target direction, all the four balls are driven to slide to the target direction, such that the user can obviously feel the weight deviation on the waist, thereby determining the next advancing direction;

when the current advancing direction is consistent with the target direction, the four balls can be uniformly distributed in the circular slideway, e.g., they are driven to slide to the front, back, left and right of his waist respectively, thereby ensuring that the user can walk normally without feeling deviation in any directions, and not only improving the user experience but also reminding the user that the current advancing direction is correct and consistent with the target direction.

The present invention further provides an apparatus for guiding the blind. The apparatus for guiding the blind comprises a memory, a processor, and a mechanical device; the memory is used for storing instructions of the processor, the processor is used for controlling the mechanical device to execute the instructions in each step of the method in the description. The apparatus for guiding the blind can be a blind guiding helmet.

Persons skilled in the art should understand that the embodiments of the present invention can be provided for a method, system, or computer program product. Thus, the present invention may be in form of all-hardware embodiments, all-software embodiments, or hardware-software embodiments. Moreover, the present invention may be in form of implementation of a computer program product on one or more computer applicable memory media (including, but not limited to, disk memory, CD-ROM, optical disk, etc.) containing computer applicable procedure codes therein.

The present invention is described with reference to the flow diagrams and/or block diagrams of the method, apparatus (system), and computer program product of the embodiments of the present invention. It should be understood that computer program instructions realize each flow and/or block in the flow diagrams and/or block diagrams as well as a combination of the flows and/or blocks in the flow diagrams and/or block diagrams. These computer program instructions can be provided to a processor of a general-purpose computer, a special-purpose computer, an embedded memory, or other programmable data processing apparatuses to generate a machine, such that the instructions executed by the processor of the computer or other programmable data processing apparatuses generate a device for performing functions specified in one or more flows of the flow diagrams and/or one or more blocks of the block diagrams.

These computer program instructions may also be stored in a computer readable memory that can guide the computer or other programmable data processing apparatuses to operate in a specified manner, such that the instructions stored in the computer readable memory generate an article of manufacture including an instruction device. The instruction device performs functions specified in one or more flows of the flow diagrams and/or one or more blocks of the block diagrams.

These computer program instructions may also be loaded on the computer or other programmable data processing apparatuses to execute a series of operations and steps on the computer or other programmable data processing apparatuses, such that the instructions executed on the computer or other programmable data processing apparatuses provide steps for performing functions specified in one or more flows of the flow diagrams and/or one or more blocks of the block diagrams.

Although preferred embodiments of the present invention have been described, persons skilled in the art can alter and modify these embodiments once they know the fundamental inventive concept. Therefore, the attached claims should be construed to include the preferred embodiments and all the alternations and modifications that fall into the extent of the present invention.

The invention claimed is:

1. A method for guiding the blind, comprising:
   determining a target direction; and
   controlling a mechanical device to shift its center of gravity toward the target direction according to the target direction,
   wherein the mechanical device comprises a balance weight, a connecting rod, and a rotating axis, the connecting rod is connected to the rotating axis, and the balance weight is located on the connecting rod.

2. The method according to claim 1, wherein one end of the connecting rod is connected to the rotating axis, and the controlling a mechanical device to shift its center of gravity comprises controlling orientation of the connecting rod that centers on the rotating axis.

3. The method according to claim 2, wherein the controlling orientation of the connecting rod that centers on the rotating axis is controlling the connecting rod to shift toward the target direction in a preset angle range.

4. The method according to claim 1, wherein center of the connecting rod is connected to the rotating axis, and said controlling a mechanical device to shift its center of gravity comprises controlling the balance weight to be located on one end of the connecting rod by the center.

5. The method according to claim 2, wherein further comprising:
   determining a current advancing direction of the user;
   controlling a distance from the balance weight to a joint between the connecting rod and the rotating axis according to relation between the current advancing direction of the user and the target direction.

6. The method according to claim 5, wherein the controlling a distance from the balance weight to a joint between the connecting rod and the rotating axis according to relation between the current advancing direction of the user and the target direction comprises:
   controlling the balance weight to slide to the joint between the connecting rod and the rotating axis when the current advancing direction of the user is consistent with the target direction.

7. A device for guiding the blind, comprising:
   a first determining module for determining a target direction; and
   a first controlling module for controlling a mechanical device to shift its center of gravity toward the target direction according to the target direction,
   wherein the mechanical device comprises a balance weight, a connecting rod, and a rotating axis, the connecting rod is connected to the rotating axis, and the balance weight is located on the connecting rod.

8. The device according to claim 7, wherein one end of the connecting rod is connected to the rotating axis, and the first controlling module is used for changing center of gravity deviation of the mechanical device by controlling orientation of the connecting rod that centers around the rotating axis.

9. The device according to claim 8, wherein the first controlling module is used for controlling the connecting rod that centers around the rotating axis to shift toward the target direction in a preset angle range.

10. The device according to claim 7, wherein a center of the connecting rod is connected to the rotating axis, and the first controlling module is used for changing center of gravity deviation of the mechanical device by controlling the balance weight to be located on one end of the connecting rod by the center.

11. The device according to claim 8, wherein further comprising:
    a second determining module for determining a current advancing direction of the user;
    a second controlling module for controlling a distance from the balance weight to a joint between the connecting rod and the rotating axis according to relation between the current advancing direction of the user and the target direction.

12. The device according to claim 11, wherein the second controlling module is used for controlling the balance weight to slide to the joint between the connecting rod and the rotating axis when the current advancing direction of the user is consistent with the target direction.

13. A blind guiding helmet comprising:
    a first determining module for determining a target direction; and
    a first controlling module for controlling a mechanical device to shift its center of gravity toward the target direction according to the target direction,
    wherein the mechanical device comprises a balance weight, a connecting rod, and a rotating axis, the connecting rod is connected to the rotating axis, and the balance weight is located on the connecting rod.

14. The blind guiding helmet according to claim 13, wherein one end of the connecting rod is connected to the rotating axis, and the first controlling module is used for changing center of gravity deviation of the mechanical device by controlling orientation of the connecting rod that centers around the rotating axis.

15. The blind guiding helmet according to claim 14, wherein the first controlling module is used for controlling the connecting rod that centers around the rotating axis to shift toward the target direction in a preset angle range.

16. The blind guiding helmet according to claim 13, wherein a center of the connecting rod is connected to the rotating axis, and the first controlling module is used for changing center of gravity deviation of the mechanical device by controlling the balance weight to be located on one end of the connecting rod by the center.

17. The blind guiding helmet according to claim 16, wherein further comprising:
    a second determining module for determining a current advancing direction of the user; and
    a second controlling module for controlling a distance from the balance weight to a joint between the connecting rod and the rotating axis according to relation between the current advancing direction of the user and the target direction.

18. The blind guiding helmet according to claim 17, wherein the second controlling module is used for controlling the balance weight to slide to the joint between the connecting rod and the rotating axis when the current advancing direction of the user is consistent with the target direction.

\* \* \* \* \*